United States Patent
Jokada et al.

(10) Patent No.: US 11,850,110 B2
(45) Date of Patent: Dec. 26, 2023

(54) METHOD OF MAKING ANTERIOR DENTAL RESTORATIONS FROM SINTERED PREFORMS

(71) Applicant: James R. Glidewell Dental Ceramics, Inc., Newport Beach, CA (US)

(72) Inventors: Marco Antonio Jokada, Diamond Bar, CA (US); David Christopher Leeson, Laguna Beach, CA (US); Vaheh Golestanian Nemagrdi, Orange, CA (US); Prabhakar Thirugnanasambandam, Irvine, CA (US); Kenad Destanovic, Mission Viejo, CA (US)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 0 days.

(21) Appl. No.: 18/161,454

(22) Filed: Jan. 30, 2023

(65) Prior Publication Data
US 2023/0172690 A1    Jun. 8, 2023

Related U.S. Application Data

(63) Continuation of application No. 17/085,239, filed on Oct. 30, 2020, now Pat. No. 11,564,773.

(60) Provisional application No. 62/929,303, filed on Nov. 1, 2019.

(51) Int. Cl.
*A61C 13/00* (2006.01)
*A61C 5/77* (2017.01)
*A61K 6/818* (2020.01)
*A61C 13/083* (2006.01)

(52) U.S. Cl.
CPC ............ *A61C 5/77* (2017.02); *A61C 13/0004* (2013.01); *A61C 13/083* (2013.01); *A61K 6/818* (2020.01)

(58) Field of Classification Search
CPC .............................. A61C 5/77; A61C 31/0004
See application file for complete search history.

(56) References Cited

U.S. PATENT DOCUMENTS

| | | | | |
|---|---|---|---|---|
| 10,133,244 B2 * | 11/2018 | Leeson | ................... | G05B 11/32 |
| 10,157,330 B2 * | 12/2018 | Azernikov | ......... | A61C 13/0003 |
| 2003/0207235 A1 * | 11/2003 | der Zel | .............. | A61C 13/0004 |
| | | | | 433/223 |
| 2005/0008887 A1 * | 1/2005 | Haymann | ................. | A61C 5/77 |
| | | | | 428/542.8 |
| 2007/0172101 A1 * | 7/2007 | Kriveshko | ............... | A61B 1/24 |
| | | | | 382/128 |
| 2009/0181346 A1 * | 7/2009 | Orth | .................... | A61C 13/0022 |
| | | | | 433/201.1 |
| 2010/0203478 A1 * | 8/2010 | Rubbert | .................... | A61B 6/14 |
| | | | | 700/98 |
| 2013/0209961 A1 * | 8/2013 | Rubbert | ............... | A61C 8/0036 |
| | | | | 433/175 |

(Continued)

*Primary Examiner* — Cachet I Proctor
(74) *Attorney, Agent, or Firm* — Charles Fowler

(57) ABSTRACT

A method is provided for shaping a custom anterior dental restoration from a preform, wherein the preform comprises a preform body and a preform stem. A method is further disclosed for generating one or more nesting positions for the restoration design within the geometry of the preform body relative to the position of the preform stem. A method is further disclosed for generating machining instructions based on the selected nesting position to optimize machining for chair-side applications.

12 Claims, 12 Drawing Sheets

(56) References Cited

U.S. PATENT DOCUMENTS

| | | | |
|---|---|---|---|
| 2013/0288026 A1* | 10/2013 | Johnson | A61C 13/00 |
| | | | 428/212 |
| 2013/0316305 A1* | 11/2013 | Carden | B23C 3/00 |
| | | | 433/202.1 |
| 2015/0125821 A1* | 5/2015 | Theelke | A61C 13/0006 |
| | | | 264/16 |
| 2016/0175076 A1* | 6/2016 | Hultgren | A61C 9/0053 |
| | | | 433/27 |
| 2017/0065380 A1* | 3/2017 | Leeson | G05B 19/4099 |
| 2017/0189146 A1* | 7/2017 | Volkl | A61C 5/77 |

\* cited by examiner

METHOD OF MAKING ANTERIOR DENTAL RESTORATIONS FROM SINTERED PREFORMS

CROSS-REFERENCE TO RELATED APPLICATIONS

This application is a continuation of U.S. patent application Ser. No. 17/085,239, filed Oct. 30, 2020, now U.S. Pat. No. 11,564,773, which claims the benefit of and priority to U.S. Provisional Patent Application No. 62/929,303, filed on Nov. 1, 2019. The entirety of each of the foregoing applications is hereby incorporated by reference in its entirety.

BACKGROUND

Ceramic materials known for use in the field of dentistry provide high strength restorations such as crowns, bridges, and the like. Some ceramic materials have flexural strength values exceeding 800 MPa when fully sintered, resulting in restorations that are resistant to chipping, breakage and wear. Material advances provide enhanced aesthetics in color and translucency while maintaining acceptable strength, and restorations may be manufactured from these materials in a cost effective manner.

Dental restorations created by computer assisted design processes may be milled by CAM processes from porous ceramic materials in the green or bisque ceramic stage, using an enlargement factor to accommodate reduction in overall size upon heating to full density. After milling, the porous restoration design is sintered to full density to produce a final restoration. Disadvantageously, the separate steps of milling the porous ceramic dental design and sintering the milled shape to form the final dental restoration, may preclude dentists from making chair-side ceramic restorations, increasing the amount of time a patient must wait for repair.

To reduce the amount of material waste to make a restoration, US2006/0204932 discloses an assemblage or library of "smart" mill blanks pre-configured into geometries and sizes that closely resemble the final dental parts. Material waste may be reduced compared to traditional mill blanks that have a single size and shape, which is desirable when using precious or semi-precious materials. The smart mill blank library is described as comprising a series of blanks with geometries that differ other than by scale, and preferably having at most, one symmetric plane. The blank is mounted in a shaping apparatus by a milling holder that has an orientation-specific attachment key for the milling machine.

Methods of making ceramic restorations from near net shape millable blanks are also known, for example, from commonly owned U.S. Pat. No. 9,597,265, which is hereby incorporated by reference in its entirety. In this document, a kit is disclosed containing millable blanks of various shapes, each shape designed to closely replicate a restoration shape thus minimizing material removal in chair-side processes. The kit comprises a variety of shapes and shades of restoration blanks, as well as chair-side software, and a chair-side milling machine to convert millable blanks into finished, contoured restorations by a dentist. Methods for making dental restorations from sintered preforms are described in commonly owned U.S. Pat. No. 10,258,440, issued Apr. 16, 2019, which is hereby incorporated by reference in its entirety.

SUMMARY OF THE INVENTION

A method for making a custom dental restoration, such as a crown, from a machinable preform is disclosed. The methods are suitable for shaping materials that have sufficient strength and hardness properties into dental restorations that may be directly inserted into the mouth of a patient without the need for a further processing step to strengthen the material after it has been shaped. Methods and apparatus described herein reduce the time required to prepare a finished dental restoration. Advantageously, fully sintered materials known for strength and durability, such as sintered yttria-stabilized zirconia, may be shaped directly into restorations in chair-side applications or in a laboratory without requiring post-shaping sintering processes. A novel sintered, shaped preform and shaping tool are described, as well as unique nesting methods, machining strategies, and tool paths.

A sintered preform from which a final, custom anterior dental restoration is shaped comprises a body of sintered material and a stem projecting from the center of the preform body. When used in a dentist office chair-side milling machine, the time to create a custom finished product is significantly reduced. Unique features of the sintered preform specifically tailored for anterior dental restoration applications include the size and shape of the preform body which accommodate most custom anterior dental restoration designs having a reduce the amount of sintered material to be removed during the process of shaping a dental restoration. Advantageously, the shape of the preform accommodates multiple options for nesting the dental restoration, and methods described herein for selecting nesting positions based on stem placement options enable the generation of unique tool paths for shaping dental restorations from sintered materials. Material preforms are provided herein comprising stems that provide novel attachments to a mandrel for inserting in a milling machine.

A method for making a custom anterior dental restoration comprises designing a custom anterior dental restoration by a known CAD (computer-aided design) process, nesting a CAD dental restoration design within a computer model of a preform body, generating tool paths from a machining strategy and the positional information of the nested restoration design, and machining the sintered preform into the final restoration. In one embodiment, a method comprises nesting the restoration design within the preform body, wherein the preform stem is positioned adjacent mesial or distal contact areas. A method further comprises generating at least two tool paths for shaping the incisal side of the anterior dental restoration or cavity side of an anterior dental restoration. In another embodiment, at least two tool paths are provided for shaping the anterior dental restoration from the incisal side and at least two additional tool paths are provided for shaping the cavity side of the restoration, wherein a single tool path is provided for a portion of the vestibular surface and a portion of the cavity surface. In a further embodiment, a machining strategy is provided for reducing the diameter of the stem adjacent the dental restoration surface.

DETAILED DESCRIPTION

A machinable, fully sintered ceramic preform is provided herein comprising novel stem and mandrel attachments. Further, a method for making a custom anterior dental restoration from a sintered ceramic preform is described herein.

Figure 1A:
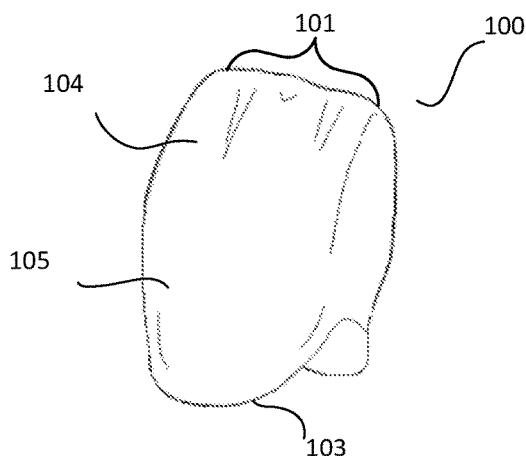
FIGS. 1A, 1B and 1C. A graphic representation of an anterior dental restoration.
Figure 1B:
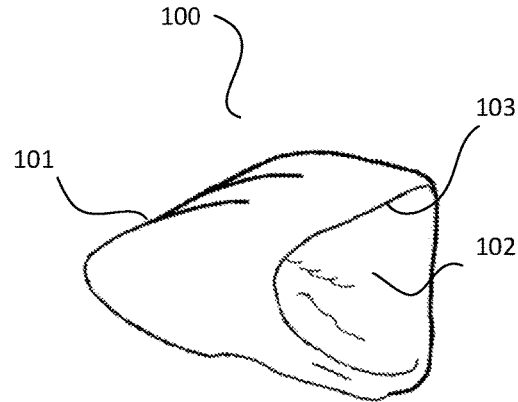
Figure 1C:
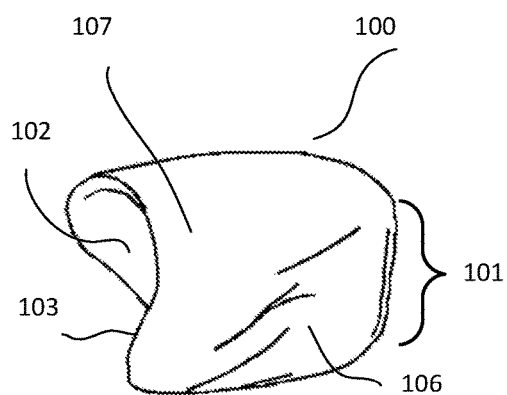

An anterior dental restoration milled from a machinable preform is illustrated in FIGS. 1A through 1C (100). Anterior dental restorations made from machinable blocks by methods provided herein replace or restore mandibular and maxillary central incisors, lateral incisors and cuspids. Anterior teeth are referred to in the Universal Numbering System (also known as the "American system") in field of dentistry by the dental notation for permanent dentition as numbers 6 through 11 on the maxilla and numbers 22 through 27 on the mandible of a patient wherein the midline is between 8 and 9 (upper) and 24 and 25 (lower). In some embodiments, the machinable fully sintered ceramic preform may also restore the natural dentition of first bicuspids and/or secondary bicuspids, referred to by the dental notation for permanent teeth as numbers 4, 5, 12, 13, 20, 21, 28 and 29.

An anterior dental restoration (100), such as crown, may have an incisal surface (101) that comes into contact with opposing teeth during occlusion. A fitting surface or cavity (102) fits on an abutment or a preparation tooth, a patient's tooth which outer surface has been prepared, e.g., by removing a portion of the natural tooth. A gingival margin (103) comprises a region or edge between the fitting surface and a vestibular surface. The vestibular surface (104) comprises the outer surface of the restoration including a labial surface (105) that faces the lips of a patient, and a lingual surface (106) facing the tongue. Vestibular side surfaces (107), include a mesial surface that is the side of the crown closest the midline of the patient's mandible or maxilla and a distal surface that is the side of the tooth farthest from the midline, both of which may be proximal contact surfaces to adjacent teeth when installed in the mouth of a patient.

Figure 2:
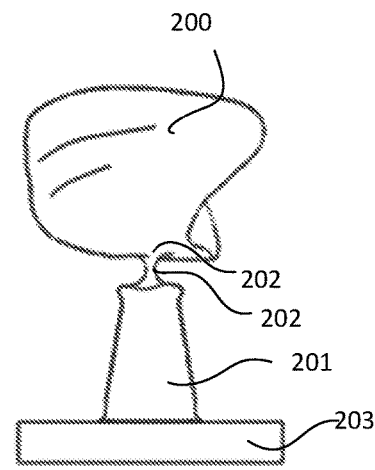
FIG. 2. A graphic representation of a dental restoration attached to a stem of a preform.

As illustrated in FIG. 2, in one embodiment, a fully sintered preform may be machined chair-side in a dentist's office into a final dental restoration (200), such as a crown. The fully sintered preform may be secured in a chair-side milling machine by an attachment means (203). The sintered dental restoration (200) may be easily separated from a preform stem (201) at a first stem end (202) that has been reduced during the milling process. After separating from the stem (201), the dental restoration (200) is secured directly into the mouth of a patient without requiring a post-process sintering step. A method is provided for machining the sintered preform into a custom final dental restoration that reduces the time required to prepare a fully sintered final dental restoration. The methods and apparatus disclosed herein comprise novel features including a unique preform design, nesting strategies, tool paths and machining strategies. In a further embodiment, a kit is provided that comprises a preform designed for anterior restorations, a grinding tool, computer programs or modules for nesting a restoration design within the preform, and machining strategies for milling a final restoration chair-side, without the need for sintering after shaping the restoration.

Figure 3A:
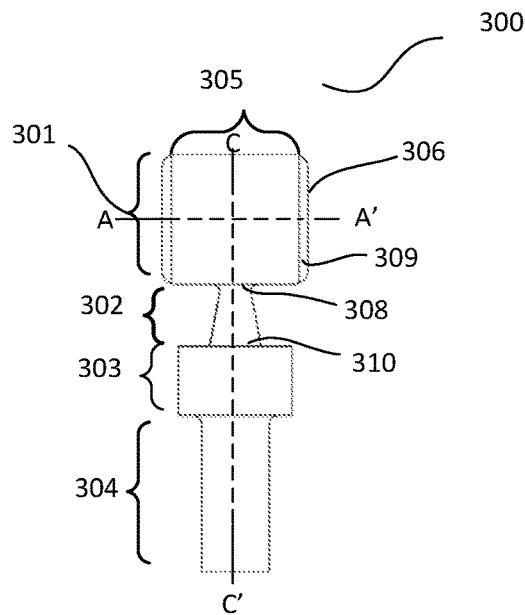
FIGS. 3A and 3B. A graphic representation of a preform on a mandrel according to one embodiment.
Figure 3B:
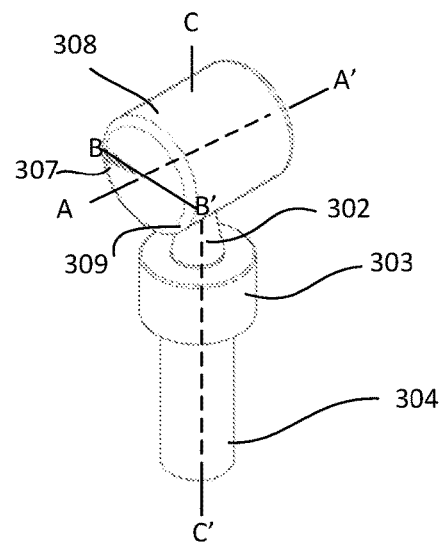

Illustrated in FIGS. 3A and 3B, one embodiment of a preform (300) comprises a machinable, fully sintered ceramic body (301) from which a dental restoration (200) is machined, and a stem (302) that projects from the body (301). A sintered preform (300) is shown that has a circular-cylindrical sintered ceramic body (301) having a curved outer surface along a cylinder length (line A-A', A-axis). In an exemplary embodiment, the preform body is positioned in chairside mill so that the axis of the cylinder length is in the same direction as the Z-axis of a shaping tool of a CNC machine. A center portion (305) of the sintered ceramic body (301) extends between bottom end (306) and a top end (307). In FIGS. 3A and 3B, the length axis (A-axis, line A-A') of the cylindrical body (301) is substantially orthogonal to the length axis (C-axis, line C-C') of the stem (302) in the y-axis direction. In this embodiment, the stem projects from a stem contact point on a substantially smooth, curved, outer surface (308) of the center portion (305) of the cylindrical body, and the stem (302) connects to the upper portion (303) of a mandrel (304) for attachment to a milling machine.

The outer diameter of a circular cross-section of the center portion (305) of a preform body from which the restoration design is shaped may be from 9 mm to 20 mm, or from 9 mm to 16 mm, or 9 mm to 16 mm, or from 9 mm to 12 mm, or at least 9 mm and less than 12 mm, such as from 9 mm to 11.5 mm, or 9 mm to 11 mm. The length of the preform body between the top end and the bottom end is sufficient to accommodate the height of most dental restoration designs when measured, for example, from the highest point of the incisal surface to the lowest point on a gingival margin; thus, the length of the preform body or the center portion of the preform body may be less than 20 mm, or less than 18 mm, or less than 16 mm, or less than 15 mm, or between about 10 mm and 20 mm. In some embodiments, the ratio of the cross-sectional diameter of the center portion to the length of the preform body is greater than 1.0:1.0, or 1:1, or less than 1:1, such as between 1:1 and 1:2.

The preform body may comprise a shape other than a cylinder, for example, an ellipsoid cylinder, a polyhedron, curved polyhedron, a cylinder with flattened surfaces, a square, a square with rounded edges, and the like. In one embodiment, the restoration design fits within the dimensions of the preform body for a complete rotation around the restoration design length axis. A preform body may have a cross-sectional geometry (parallel with top and bottom surfaces) with an inscribed circle diameter greater than 9 mm and a circumscribed circle diameter less than 12 mm at the stem contact point.

Figure 5:
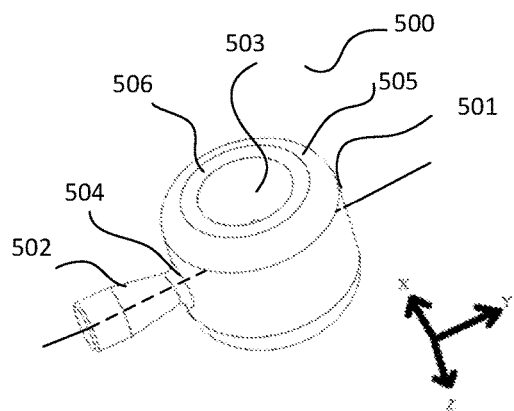
FIG. 5. A graphic representation of a preform body and stem according to one embodiment.
Figure 6:
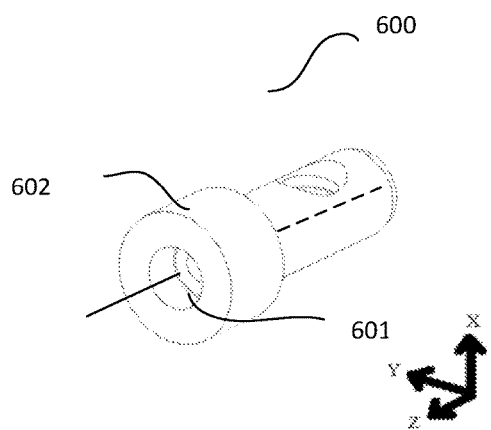
FIG. 6. A graphic representation of a mandrel according to one embodiment.
Figure 9A:
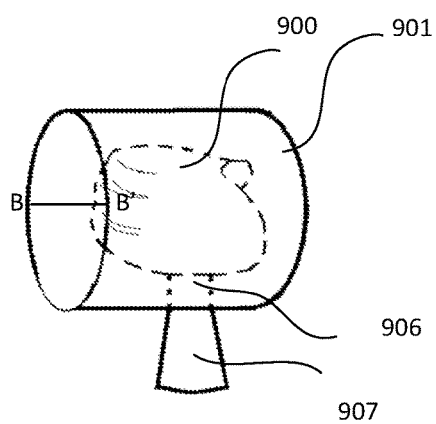
FIGS. 9A, 9B and 9C. Graphical representations of nesting an anterior restoration design within a model of preform.

In some embodiments, the preform body is solid and the top end surface and/or bottom end surface are flat (FIG. 9A). As illustrated in FIGS. 3A and 3B, optionally the top and bottom end surfaces also comprise a shaped edge (309). For example, a preform may comprise a chamfer or fillet between the curved outer surface (308) of the preform body (301) and top end surface (307) and/or bottom end surface (306). As illustrated in FIG. 5, a filleted edge (505) may surround the bottom end surface (506). Advantageously, forming a dental restoration from a preform having a shaped edge, may require less material removal, shortening the shaping time.

As exemplified in FIG. 5, optionally, the preform body (501) comprises a preform body cavity (503) that begins at a top surface, bottom end surface (506), or both top and bottom, and extends into the preform body wherein a preform body cavity surface is accessible by a shaping tool. The shape of each preform body cavity may comprise, but is not limited to, an inverted cone, dome, cylinder, trough, or the like, or may have an irregular shape. An opening or breakout geometry of the preform body cavity may have a width (or diameter, for example where the breakout area is circular) that is between about 20% and 80% of the outer diameter or width of the center portion of the preform body. About 50% to about 80% of the surface area of a top end surface, a bottom end surface, or a center portion cross-section, comprises the break-out dimension. The approximate preform cavity depth extending from the end surface into the preform body may be between 5% and 50% of the length of the preform body.

As exemplified in FIGS. 3A and 3B, the preform stem (302) length (along C-axis) is orthogonal to the length of the cylindrical body (along A-axis). In some embodiments, the stem length is within about 30 degrees or within about 45 degrees of orthogonal, relative to the body. In one example, a first stem end (308) extends from the center portion (305) of a cylindrical body (301), and the preform stem contact point is approximately equidistant between the bottom end (306) and the top end (307) of the preform body. In some embodiments, prior to shaping the sintered preform, the length of a preform stem is greater than the width of the stem at the first stem end (308) proximate the cylindrical body. For purposes herein, width may be used interchangeably with diameter, for example, in embodiments in which the stem has a circular cross-section. The preform stem length may be between about 3 mm and about 12 mm, or between about 3 mm and about 10 mm prior to milling the restoration. In some embodiments, the preform stem length may be greater than about 3 mm, or greater than about 4 mm, greater than about 5 mm, greater than about 6 mm, or greater than about 8 mm. In one embodiment, the width (diameter) of the first stem end (308) is less than the width (diameter) of the second stem end (310) proximate the top portion (303) of the mandrel (304). The width (diameter) of the first stem end may be about 1 mm to about to about 4 mm, or from 1 mm to about 3 mm, or about 1.5 mm to about 3 mm, or 1.5 mm to about 2.5 mm, or less than about 4 mm , or less than about 3 mm, or less than about 2.5 mm. In some embodiments, the ratio of stem length to the first stem end (308) width or diameter (proximate the preform body) is greater than about 1.5:1, or greater than about 2:1, or greater than about 3:1.

In one embodiment, the preform stem length is greater than the diameter of the shaping tool. The distance between the preform body (301) and the top portion of the mandrel (303) provides a space equivalent to the length of the stem for entry of a shaping tool near the first stem end (308), without the tool tip contacting the sintered preform material, and thereby reducing tool wear. The flex strength of the preform stem (302) at the first stem end (308) is sufficiently high to support the sintered preform (300) during machining from a sintered state, and sufficiently low for the finished restoration to easily be broken off from the stem, for example, by hand. The preform stem shape may be a cylinder, tapered cylinder, cone, prism or the like, and the stem is connected to the center portion of the preform body at the stem contact point by a first stem end.

Figure 4:
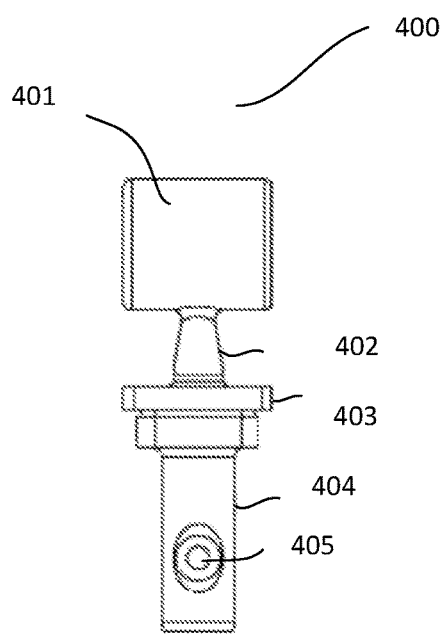
FIG. 4. A graphic representation of a preform on a mandrel according to one embodiment.

Milling machines, such as chair-side mills suitable for milling the sintered preform into a final dental component have at least 3 axes, such as a 3+1 axis CNC machine. A suitable chair-side milling machine includes, but is not limited to the TS150™ chair-side milling system (IOS Technologies, San Diego, CA), or a milling machine as described in commonly owned U.S. Pat. No. 10,133,244, which is incorporated by reference herein in its entirety. The sintered preform (400) may be secured within a milling machine by fastening the preform to a mandrel. In one embodiment illustrated in FIG. 4, a preform (400) comprising a millable body (401) and preform stem (402) may further comprise an attaching member (403) for attaching the preform to a mandrel (404). The attaching member (403) may be shaped as a rectangle, circle, or square, having a substantially flat surface for adhesive attachment to a mandrel. The mandrel (404) may be secured within a milling machine with a locking mechanism (405), such as locking pin and hole elements.

In a further embodiment illustrated in FIGS. 6, 7A, 7B, 7C and 8, the preform stem is inserted into a mandrel (600) through a hole (601) on the top portion (602) of the mandrel, and secured, for example, by an interference fit, such as a press or friction fit, adhesive or mechanical locking mechanism. In one embodiment of a preform (700), exemplified in FIGS. 7A, 7B and 7C, the preform body (701) is attached to a preform stem (702) having a second stem end (703) that comprises at least one groove (704), at least one ridge (706), or both, on the outer surface of the second stem end (703), for attachment to a mating end of the mandrel. The groove (704) and/or ridge (706) may engage with a complementary convex or convex surface feature on the inner surface of the mandrel to form a locking mechanism. In an alternative embodiment, the at least one ridge (706) is comprised of sintered zirconia cuts or depresses the inner surface of a mandrel made from a softer material, such as a polymer (e.g., nylon) forming an anti-rotational press fit connection.

Figure 8:
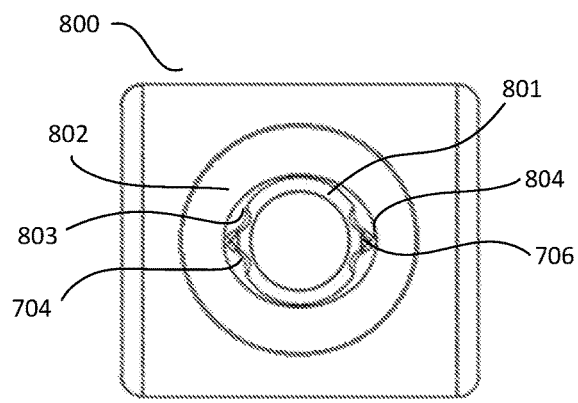
FIG. 8. A cross-sectional representation of a preform stem in a mandrel according to one embodiment.

In a further embodiment, attachment between the preform stem and the mandrel may be strengthened by the addition of an adhesive. Optionally, surface features, such as one or more channels (707) or grooves (704), are milled into the stem to hold adhesive and increase the bonding surface area of the stem outer surface area. FIG. 8 illustrates a cross-sectional view of an interference fit between the preform stem (801) engaged within a mandrel (802) wherein a portion of the mandrel inner surface (804) is deformed by a ridge (706) forming an anti-rotational fit, and an adhesive connection (800) comprising an adhesive within stem channels (707) and within a gap (803) between the stem (801) and mandrel (802). Suitable adhesives include, and are not limited to, light and heat curable adhesive resin, such as a two-part epoxy composition (e.g., UHU® Plus 300, two-part epoxy resin, heavy duty applications, UHU GmbH & Co., Bühl, Germany).

The anterior dental restoration design may be created manually by an operator, or automatically proposed, in a dental restoration CAD system. Known design systems, such as IOS FASTDESIGN™ System (IOS Technologies, San Diego, CA), are suitable for designing dental restorations for use herein, as well as methods disclosed in commonly owned U.S. Pat. Pub. 2015/0056576, U.S. Pat. No. 10,248,885, and U.S. Pat. No. 10,157,330, the disclosure of each is hereby incorporated herein by reference in the entirety. Anatomical information about the patient's tooth preparation, and optionally, surrounding teeth and the patient's original tooth structure, may be obtained from an intraoral scan or scans of physical impressions taken from the patient. Data are collected and stored in a computer or computer storage media to form a digital restoration design. In further embodiments, methods are provided for generating machining instructions to mill the anterior dental restoration from the millable preform body in CAD/CAM-based systems.

A computer-implemented method for nesting a computer model of the patient-specific restoration within a computer model of the preform geometry is provided. The computer model of a patient's dental restoration design may be selectively nested in one or more optional positions within a computer model of the preform to establish optimal machining conditions for a selected CNC machine, milling or grinding tool and/or machine coolant system, and preform materials. Positional data of the nested restoration design may be provided to the CAM system to calculate tool paths from machining strategies, including lace direction, XY step over, maximum Z increments, feed rates, coolant parameters, and the like, based on the milling machine selected and properties of the grinding tool, as further described herein.

Figure 9B:
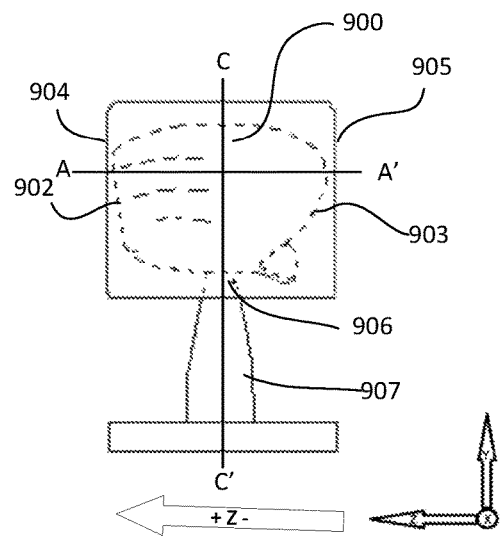
Figure 9C:
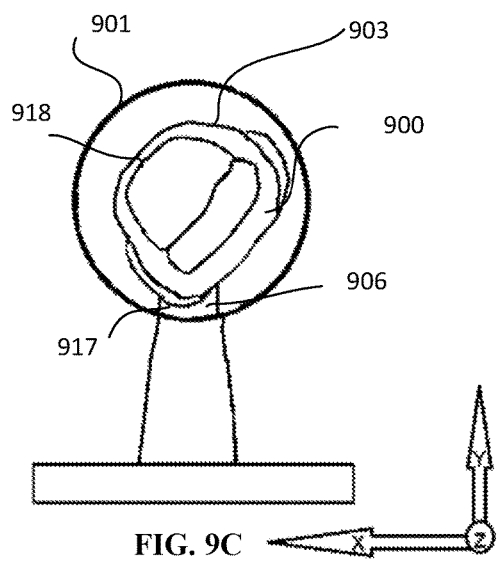

As illustrated in FIGS. 9A through 9H, a nesting method comprises arranging the restoration design (900) and the preform body (901) at a rotation around line A-A' which is in the Z-axis direction of a grinding tool when placed in a milling machine. In one embodiment, as illustrated in FIGS. 9A through 9C, a model of the dental restoration design (900) may be nested within the geometry of a preform body (901) so that the incisal edge (902) and the gingival margin (903) of the restoration design are adjacent opposite ends, the top end (904) or bottom end (905), of the preform body (901).

In one embodiment, as exemplified in FIGS. 9C through 9H, a nesting option may be selected based on the location of the stem (907) relative to the restoration design. The method further comprises designing a stem upper portion of (906) within the body of the preform body (901) that will be milled during the restoration milling process. During the nesting process, a position of the restoration (900) around the A-axis may be selected so that the stem upper portion (906) contacts the lingual surface (FIG. 9E, 908) or labial surface (FIG. 9G, 9H) of the restoration design. A minimum distance may be established between the outer surface of the stem and the incisal edge or gingival margin.

Figure 9D:
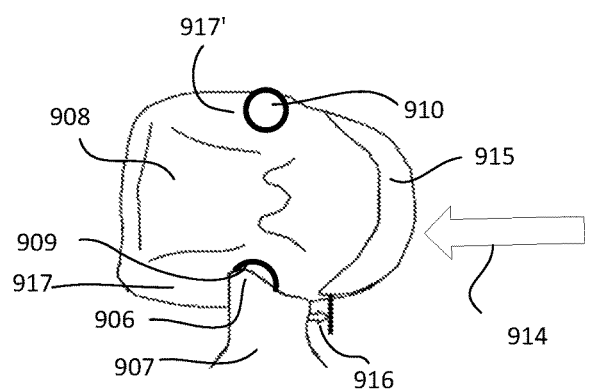
FIGS. 9D through 9H. Graphical representations of exemplary nesting positions of an anterior restoration design relative to a stem of a model of millable preform.
Figure 9E:
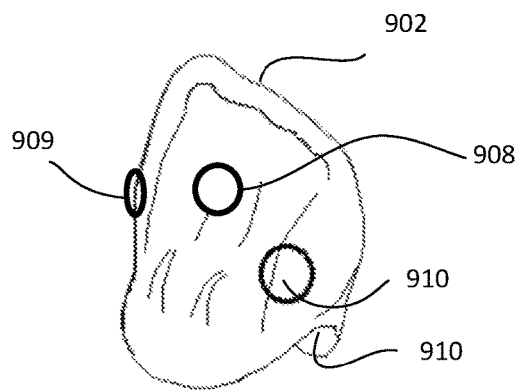

In an embodiment illustrated in FIGS. 9D and 9E, the restoration design is nested within the geometry of the preform so that the stem upper portion (906) is located lingually, adjacent a mesial side or distal side, such as on, or adjacent, a marginal ridge (917, 917') between a lingual surface and mesial or distal side (909, 910), or near a proximal contact area with an adjacent tooth. The mesial side as used herein refers to a side or surface of the tooth closest to the midline, and the distal side as used herein refers to a side or surface of the tooth farthest from the midline. A proximal contact area refers to the tooth surface that touches an adjacent tooth in the same arch. A distal proximal contact may contact the mesial side of a more posteriorly positioned adjacent tooth; the mesial proximal contact may contact the distal side of an anteriorly oriented adjacent tooth. Contact areas may be identified by a technician, or automatically identified by the restoration design software.

Figure 9F:
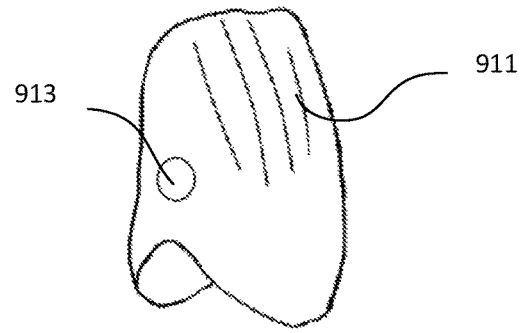
Figure 9G:
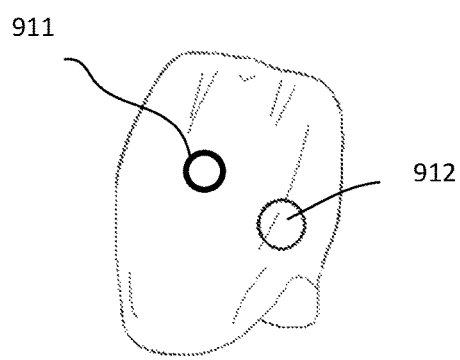
Figure 9H:
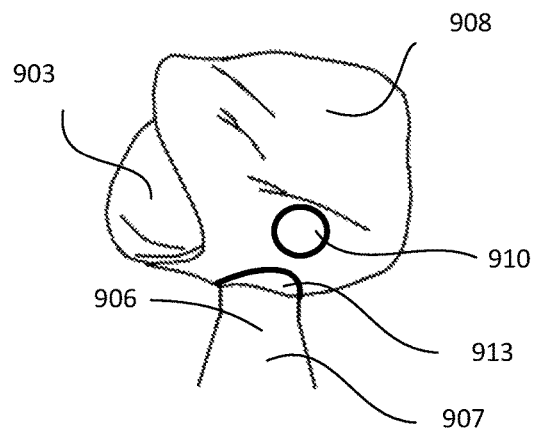

In embodiments illustrated in FIGS. 9F, 9G and 9H, the restoration design is nested within the geometry of the preform so that the upper portion of the stem is located labially, such as between the labial surface and mesial or distal sides (912, 913), or on a mesial side or distal side.

In another embodiment, a milling machine is provided with a coolant delivery system for delivering coolant, such as water, to cool the grinding tool and/or milling surface during the milling process. Nesting options on the lingual or labial surfaces, or adjacent proximal contact areas, optimize for coolant delivery to the cavity (903). In one embodiment, as illustrated in FIG. 9C and FIG. 9D, a nesting option is selected by aligning the delivery angle of the coolant (914) with the cavity opening (915) of the dental restoration design. In one embodiment, a nesting option is selected wherein the delivery of the coolant is directed toward the cavity adjacent the curved lingual surface (918), as illustrated in FIG. 9C. In an alternative embodiment, a nesting option is selected wherein the delivery of the coolant is directed toward the side of the cavity adjacent the curved labial surface. By nesting the restoration design within the preform so that the stem contact point is, for example, on a labial or lingual surface, or between a labial or lingual surface and a mesial and/or distal side, the direction of the coolant flow into the cavity of the restoration may be optimized.

Nesting threshold parameters may be established that provide for a minimum distance between the outer surface of the preform body and the outer surface of the anterior dental restoration design, or between the surface of the stem and the gingival margin. As illustrated in FIG. 9D, a distance (916) between the stem outer surface and the gingival margin may be at least 0.5 mm, or at least 1 mm, or between 0.5 mm and 3 mm. Optionally, a distance (917) between the restoration design outer surface and the edge of the preform body may be at least 0.2 mm, or at least 0.5 mm, or at least 1 mm, as illustrated in FIG. 9C. Further, a minimum distance between the restoration design surface and the stem may be established, for example, to be about 0.5 mm to 1.5 mm. The restoration design may also be translated along one or more of A–, B–(along line B-B') and C-axes of the preform to achieve nesting parameters within the geometry of the preform model. For example, translation along the A-axis adjusts the distance between the incisal edge or gingival margin of a restoration design and top end or bottom end of the preform body. Positional data of the nested restoration design may be provided to the CAM system to calculate tool paths to shape the final restoration from the preform.

A computer implemented method for nesting a restoration design is provided that comprises determining if the restoration fits within the geometry of a computer model of the preform body; nesting incisal edge and gingival margin of the anterior restoration design along the A-axis, adjacent either a top or bottom end of a preform body; establishing minimum distance parameters between the restoration design and the preform body surface, the stem and the restoration surface, and the outer surface of stem and the gingival margin. If the minimum distance between the restoration design outer surface and the preform body surface cannot be achieved in any nesting position, the program may be exited so that a different option may be pursued by the dentist, such as a modified restoration design or use of an alternative preform body. If the restoration design fits within the preform geometry, at least one nesting option is identified, as follows. The method further comprises positioning the stem on a labial side, optionally, adjacent a mesial or distal contact area, or alternatively, on a lingual side, optionally, adjacent a mesial or distal contact area. In one embodiment, the method further comprises determining the angle of the coolant flow and selecting a stem position that optimizes coolant flow onto or into the cavity and maintains minimum distance parameters.

A method is provided for obtaining a machining strategy for a selected nesting position that comprises two or more machining steps to shape a restoration based on the nested design. Each machining step may comprise a tool path for machining a portion of the restoration including machining strategy elements such as lace direction, XY step over value, maximum Z increments, feed rates, coolant parameters, and the like. Tool paths may be established using linear interpolation methods based on XYZ machining positions, and spacing between tool path lines or passes may be selected to optimize machining conditions.

Figure 10:
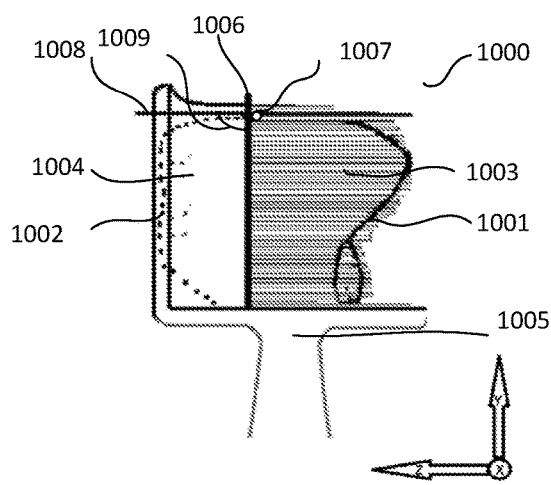
FIG. 10. A graphical representation of a lacing tool path for a vestibular surface of an anterior dental restoration design.

In an exemplary embodiment of FIG. 10, a tool path (1000) overlaying a portion of the cavity side of a restoration design follows a lacing, or zig-zag, pattern. More than one tool path may be provided for shaping the restoration. For example, a first tool path may be provided for shaping a portion of the restoration design closest to the gingival margin (1001), herein referred to as the restoration cavity side (1003) of the anterior dental restoration. A second tool path may be provided for shaping a portion of the anterior restoration adjacent the incisal edge (1002), herein referred to as the incisal side (1004) of the anterior restoration. A further tool path may be provided to reduce the diameter of the stem (1005) adjacent the surface of the dental restoration to facilitate separation of the stem from the restoration.

Figure 11A:
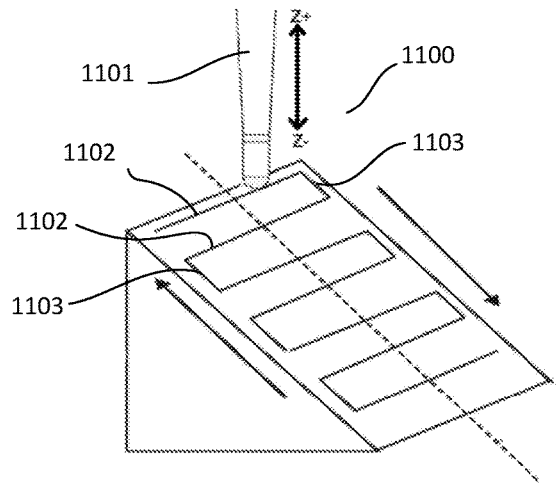
FIGS. 11A, 11B and 11C. Graphical representations of a portion of a tool path across a slope according to one embodiment.

Exemplified in FIG. 11A, a lacing pattern (1100) comprises adjacent parallel tool path lines extending across a milling surface as a milling tool (1101) moves in a X-negative (X−) or X-positive (X+) direction, that are separated by a step over distance, for example, in a Y-negative (Y−) or Y-positive (Y+) direction orthogonal the tool path lines relative to the milling surface. The XY step over distance (1103) distance providing planar spacing between parallel lines of the lacing pattern may be an arbitrary increment, for example, based on tool (1101) dimensions, such as the diameter of the tool tip. Alternatively, an established tool path step over distance in a Y-axis direction between sequential lines may be independently decreased to insert additional lines in the tool path for a portion of the tool path. In one embodiment, a XY step over is less than 11 μm, or less than or equal to 10 μm, such as between 7 μm and 10 μm, or 7 μm and 9 μm.

Figure 11B:
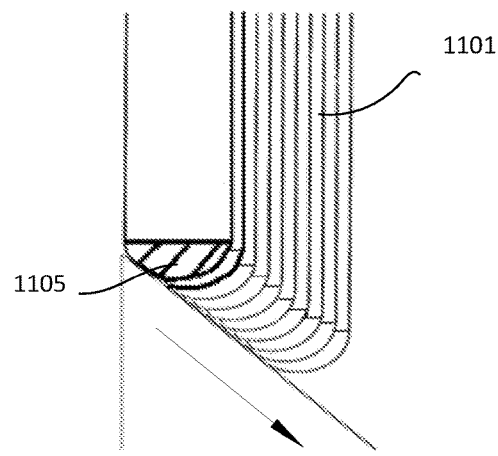
Figure 11C:
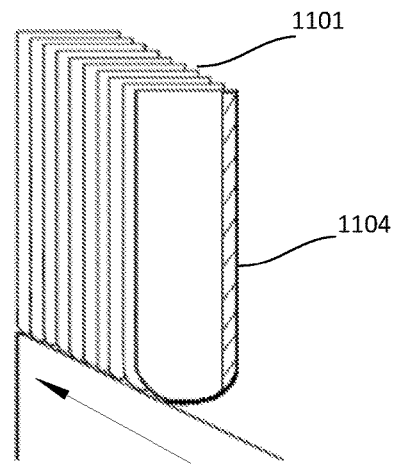

Controlling material removal by the tool tip or the tool side to advantageously reduce excess wear on the tool, may be achieved by controlling the tool movement in the Z-positive (Z+) direction (moving upwardly relative to a milling surface) or in a Z-negative (Z−) direction (projections through the milling surface). FIGS. 11B and 11C illustrate cross-sectional representations of the lacing tool path of FIG. 11A (through the dotted line), and the movement of a tool (1101) across a slope. Step over distances between adjacent lines incrementing in a 'down-hill' movement across a slope (FIG. 11B), with projections of the tool through the tool path in a Z-negative direction, are illustrated in FIG. 11B. 'Up-hill' movement is illustrated in FIG. 11C, as the grinding tool (1101) moves through the tool path toward Z-positive, and the tool is lifted away from the surface to be machined. Movement in the Z-positive direction results in material removal by a tool side surface (1104) reducing material removal by a tool tip (1105). Material removal by the tool tip (1105) may result in heating of the tool, wear on the tool tip, and excessive wear on the grinding media, such as diamonds embedded in an alloy coating on the tool shank. A threshold step over value may be established for a maximum distance between two tool path lines in the Z-negative direction (e.g., a maximum Z increment value in a Z-negative direction). Where the distance between two sequential lines in one area of the tool path sequence exceeds a maximum Z-increment, the XY step over distance (1103) between adjacent lines may be decreased to insert additional tool path lines, decreasing the Z-increment between lines, until the threshold value in the Z-negative direction is met or not exceeded. In one embodiment, a maximum step over between parallel lines in the Z-negative direction is less than 11 μm, or less than 10 μm. In some embodiments, the Z-negative step over value is between 5 μm and 10 μm, or between 5 μm and 10.5 μm.

Methods are provided that minimize the percentage of Z-negative direction movement of a grinding tool by the selection of nesting positions of a restoration design within the preform geometry, and the generation of tool paths from the selected nesting position. For each nesting option, a negative slope value may be calculated for a given tool path. Negative slope values are calculated as the percentage of a restoration design surface area that is determined to have a negative slope greater than a threshold angle, such as 10°, 15°, 20°, or 30°, or greater, when viewed from the machining direction. Optionally, a negative slope value may be calculated for a specified surface, such as a portion of the restoration cavity side surface, or a portion of the restoration incisal side surface. A negative slope value may be calculated as the sum of the percentage of surface area having a negative slope greater than a threshold angle for a specified surface. The surface area with negative slope corresponds to the surface area in which shaping is performed by down-hill (Z-negative) machining of the tool at an angle greater than or equal to a threshold angle. For example, in one embodiment using an stl. file format, a surface of a restoration design may be analyzed to determine what percentage of a triangulated surface geometry is sloped greater than a threshold value relative to normal, when viewed from a machining direction. A nesting position having a low negative slope value, corresponding to the percentage of surface area with negative slope less than or equal to a specified threshold value, may be selected as the nesting position from which to calculate a tool path. Nesting software may be separate from the dental restoration design software or may comprise a module of the design software that may be automatically implemented upon completion of the restoration design. Nesting information, comprising positional data of the restoration relative to the preform body, and the stem relative to the dental restoration, may be used for computing tools path sequences.

Machining strategies based on selected nesting options may comprise tool paths that are split based on dimensional limits of the milling machine and tool. As illustrated in FIG. 10, a flat separator (1006) between restoration incisal side (1004) and cavity (1002) side coincides with the dimensional limits of a 3-axis milling machine and the milling tool where the restoration surface angles (1009) away from the parting line along the Z-axis, when viewed from the restoration cavity side. In one embodiment, cavity side and incisal side machining steps are separated at a point (1007) of the Z-axis (1008) coincident with a parting line between incisal and cavity sides that is farthest from the gingival margin.

Figure 12A:
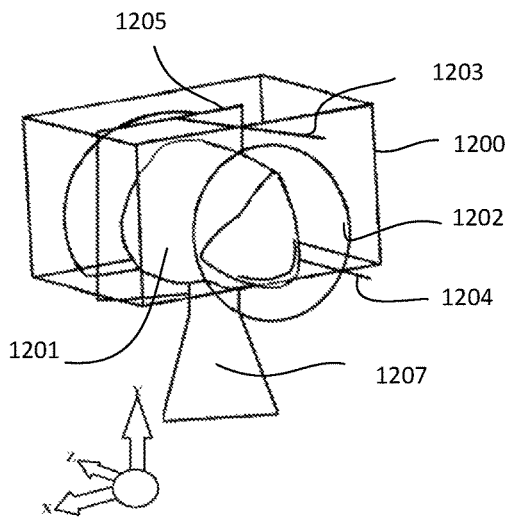
FIGS. 12A through 12G. Graphical representations of machining strategies for generating tool paths for an anterior dental restoration.
Figure 12C:
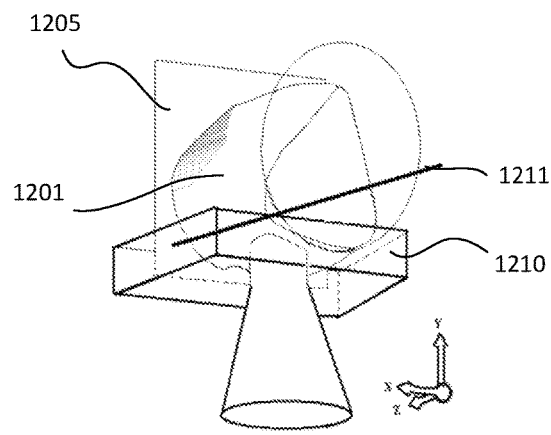
Figure 12B:
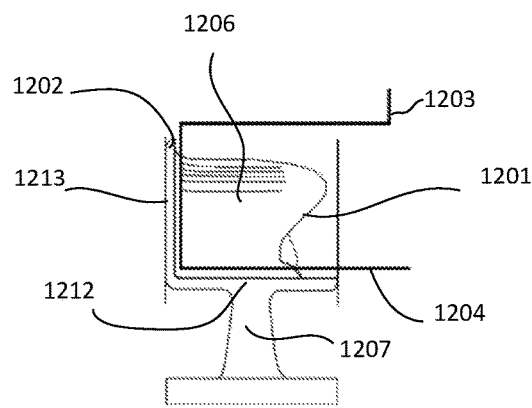
Figure 12D:
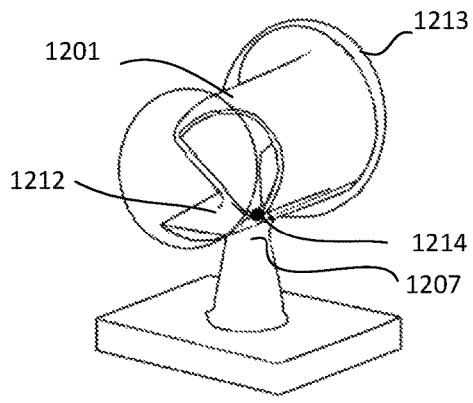
Figure 12E:
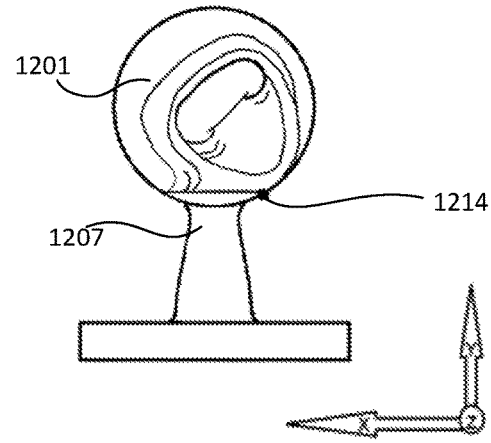

In one embodiment, FIGS. 12A through 12G further illustrate a machining strategy for a preform (1201) that is split at a flat separator (1205) between the cavity side (1201) and incisal side (1213). The cavity side (1201) of the restoration design may be split into two or more machining steps (1200, 1210) having separate tool paths. In one embodiment illustrated in FIG. 12A, a first machining step (1200) having a first tool path is provided to shape a first portion of a cavity side (1206) of the restoration that is opposite the stem (1207), and a second machining step (1210) having second tool path shapes a second portion of a cavity side (1212) that is adjacent the stem. Tool path tool entry points (e.g., 1203, 1211) and a tool stop point (e.g., 1204) are shown in FIGS. 12A and 12C.

Figure 12F:
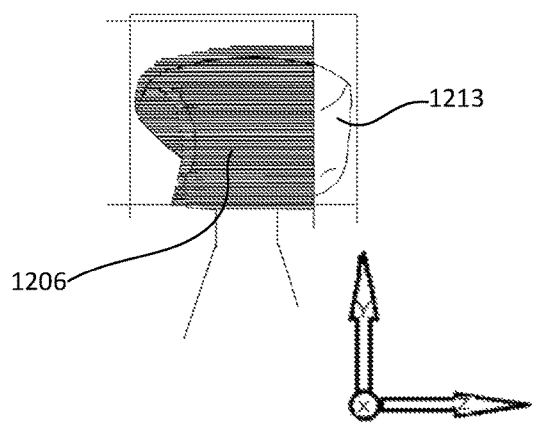
Figure 12G:
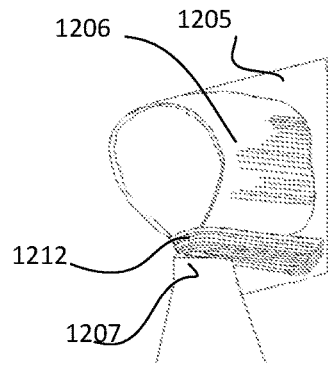

The tool path sequence for machining first and second portions of the cavity side may be split at an arbitrary point relative to the Y-axis, or the tool path sequence may be split based on positional information of the nested restoration, selected to optimize machining parameters described herein. In one embodiment, as exemplified in FIGS. 12D and 12E, first and second cavity side tool paths are separated at a point (e.g., 1214) relative to the Y-axis in which the surface of the first cavity side opposite the stem slopes negatively toward the stem (1207) greater than a maximum angle. In one embodiment illustrated in FIGS. 12F and 12G, the first and second portions of the cavity side comprise lacing tool paths with line lengths extending in the Z-axis direction over the vestibular surface, or perpendicular to the flat separator (1205), minimizing material removal by the tool tip and maximizing material removal by the tool side surface. In a further embodiment, as illustrated in FIG. 12F a single lacing tool path for the first portion of the cavity side (1206, opposite the stem) is applied to most of the cavity side vestibular surface and the fitting surface of the cavity, and a second lacing tool path, illustrated in FIG. 12G, may be provided for the second portion of the cavity side (1212, adjacent the stem) which consists of the remainder of the cavity side vestibular surface and optionally, a portion of the stem.

Figure 13A:
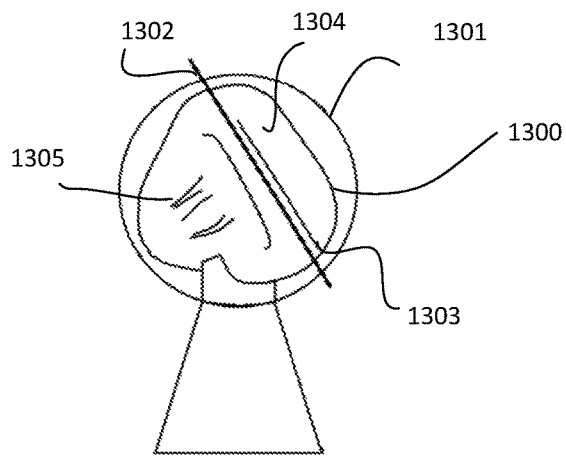
FIGS. 13A through 13D. Graphical representations of machining strategies for milling an anterior dental restoration from a preform.
Figure 13B:
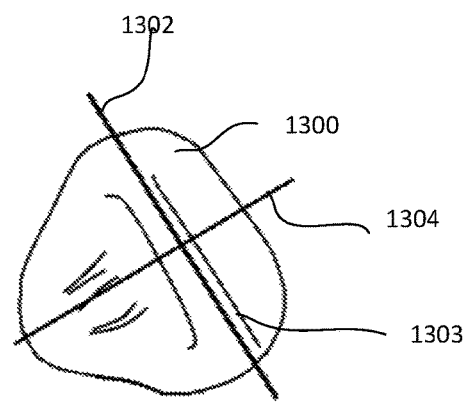
Figure 13C:
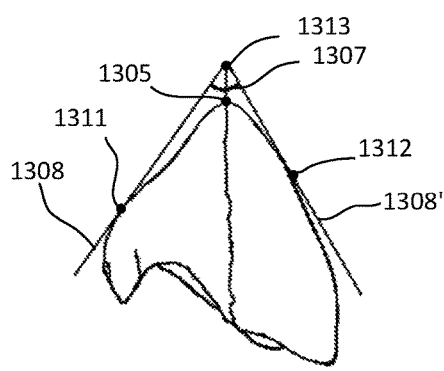
Figure 13D:
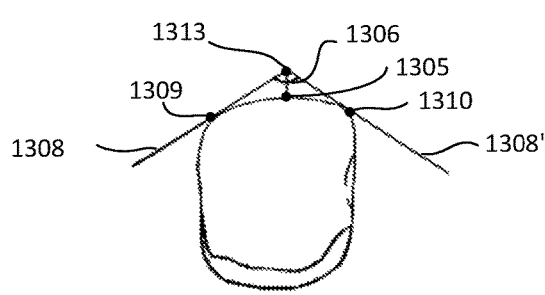

Further, a method is provided for separating a tool path sequence for the incisal side of an anterior dental restoration that is nested, for example, according to FIGS. 9A and 9B. In some embodiments, tool paths for milling the incisal side of the restoration (1300) are separated at the incisal edge (1303), for example, parallel (1302) or orthogonal (1304) to the incisal edge, to minimize material removal in the Z-negative direction. FIGS. 13A through 13D illustrate an anterior restoration design (1300) nested within a preform body (1301), and methods for separating first and second tool paths of an incisal side comprises detecting a topmost point (1305) on the incisal edge of the crown. Angles (e.g., 1306, 1307) formed from lines (e.g., 1308, 1308') intersecting a vertex (1313) at a distance (e.g., 1 mm) above the topmost point (1305) and extending to points (e.g., 1309, 1310) on opposite outer surfaces of the design, may be identified to determine the smallest angle. The smallest angle may be selected and a line between the opposite points of the intersecting lines may be used separate tool paths. In one embodiment, opposite points at mesial and distal surfaces (1309, 1310) of intersecting lines (1308, 1308') define a line of separation (1302) parallel to the incisal edge (1303) that separates tool paths between lingual and labial surfaces, as illustrated in FIGS. 13A and 13D. In an alternative embodiment, opposite points at lingual (1311) and labial (1312) surfaces of intersecting lines (1214, 1214') define a line of separation (1204) that is orthogonal the incisal edge (1203) separating the tool paths between mesial and distal sides of the restoration, as illustrated in FIG. 13C.

Figure 14A:
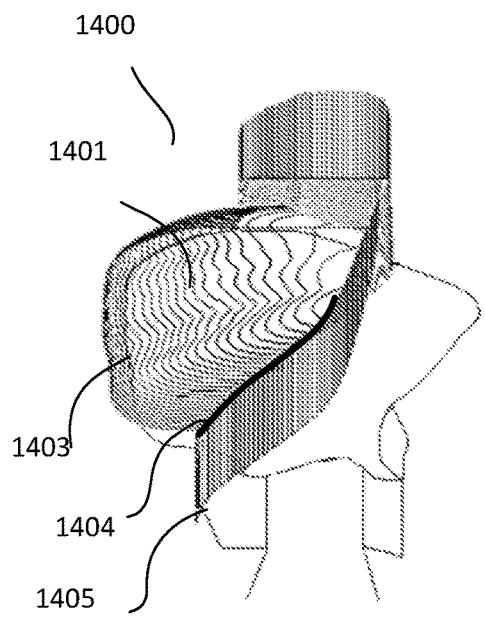
FIGS. 14A and 14B. A graphical representation of machining strategies for milling labial and lingual surfaces of an anterior dental restoration.
Figure 14B:
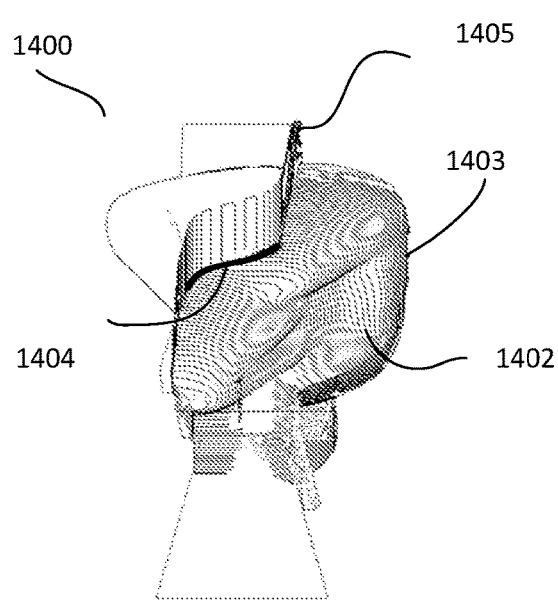

As exemplified in FIGS. 14A and 14B, first and second lacing tool paths separated at an incisal edge (1403) are illustrated for shaping the incisal side of an anterior restoration design. A first lacing tool path is provided for the labial (1401) surface and a second lacing tool path is provided for the lingual (1402) surface. In one embodiment, machining instructions for shaping the incisal side of a dental restoration comprise a first tool path for shaping the labial surface (1301) and a second tool path for shaping the lingual surface, wherein both tool paths have sequential tool path line lengths parallel the incisal edge (1403), that extend between mesial and distal sides of the tooth to the parting line.

Tool paths may follow the parting line (1404) between the incisal edge and the gingival margin, and extend to tool offset positions (e.g. 1405). The parting line (1404) follows the contour, or largest dimension of the outer surface, of the restoration when viewed from the incisal edge. The first and second tool paths may overlap the incisal surface or the parting line for a distance of, for example, 0.3 mm to 2 mm to provide a smooth transition. Tool offset positions may be calculated based on the dimensions of the preform body and stem.

Figure 15A:
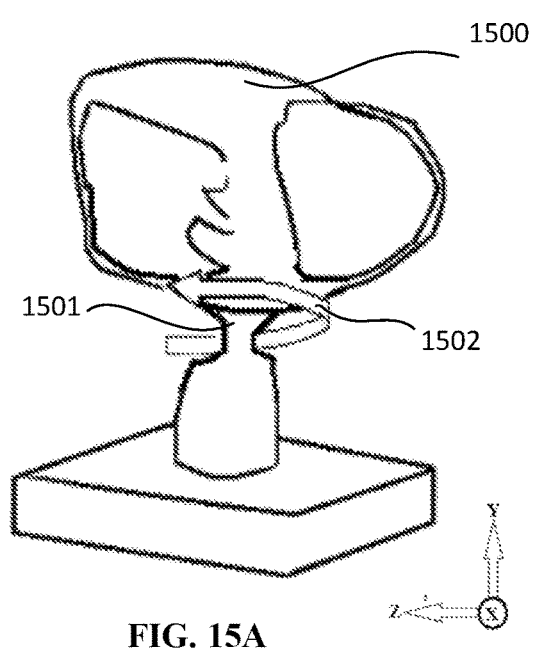
FIGS. 15A through 15B. Graphical representations of an exemplary machining strategy for reducing a stem of a preform.
Figure 15B:
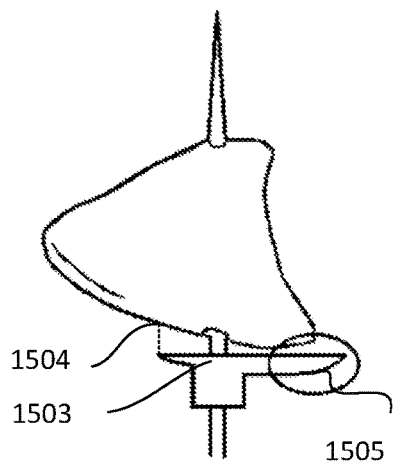

A method is also provided for reducing the stem geometry to facilitate separating the stem from the milled restoration. As exemplified and illustrated in FIGS. 15A, a rotary tool path around a first stem end (1501) adjacent the dental restoration (1500) reduces the stem diameter to enable the restoration to be snapped off the stem by hand or by a handheld tool. In one embodiment, machining steps comprising a rotary tool path (1502) around the stem form a plurality of horizontal slices that are perpendicular to the length axis of the stem. The distance of the tool path boundary from the stem may increase where the stem attaches to the restoration on an angled surface of the restoration. For example, as illustrated in FIG. 15B, a boundary (1503) for a rotary tool path that extends to reach a point (1504) of the crown high along the Y-axis, may unnecessarily extend over a portion of the restoration profile where the crown is lower on the Y-axis (1505).

Figure 16A:
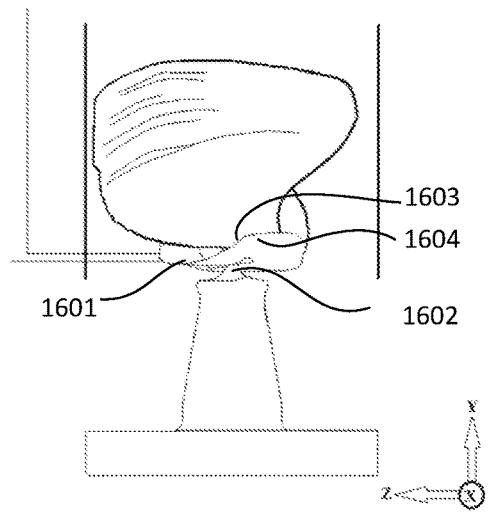
FIGS. 16A through 16D. Graphical representations of an exemplary machining strategy for reducing a stem of a preform.
Figure 16B:
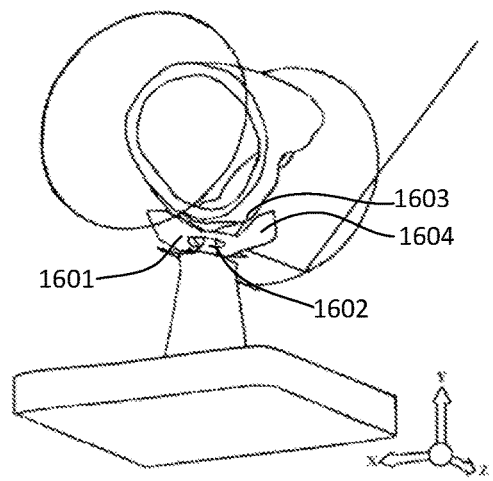
Figure 16C:
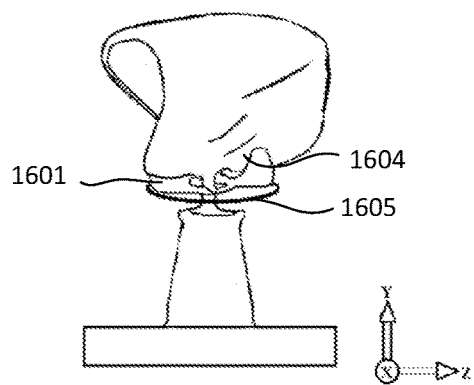
Figure 16D:
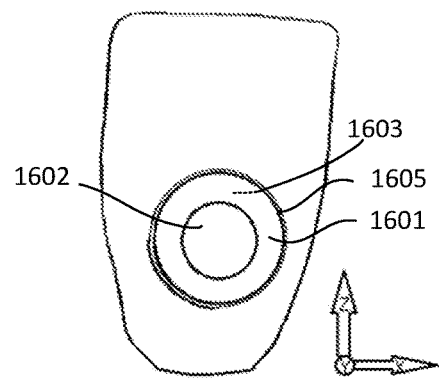

In an alternative embodiment as illustrated in FIGS. 16A and 16B, a rotary tool path (1601) is provided wherein rotary movement of the milling tool around the stem (1602) is synchronized with movement of the tool in the Y-axis direction. To reduce the size of the tool path boundary, a rotary tool path is provided where as the tool rotates around the stem, Y-axis direction tool path movement (1604) simultaneously follows the restoration surface (1603) that is adjacent the stem. In one embodiment, as illustrated in FIGS. 16C and 16D, a rotary tool path further comprises a containment border (1605), where the boundary of the rotary tool path does not extend past the containment border. The diameter of the containment border (1605) may be calculated as the sum of the diameter of the stem at the surface of the restoration and the radius of the milling tool (for example, 0.5 mm to 1 mm, such as 0.8 mm), and optionally, a tolerance distance may be added to the diameter. The distance of the movement of the tool in the Y-axis direction during a rotation may be increased or decreased so that the boundary of the tool path complies with the containment border.

In one embodiment, a method for generating machining instructions for an anterior restoration comprises: 1) nesting an anterior restoration design within a computer model of a preform body wherein the preform body comprises a cylindrical shape having a stem projecting from the curved outer surface, wherein nesting comprises: a) positioning the incisal side of the restoration design adjacent a first circular end of the preform and the cavity side adjacent the second circular end; and b) positioning a first stem end adjacent a labial or lingual side or a restoration design, optionally adjacent or on a mesial or distal side; and 2) generating machining instructions comprising a) a first tool path for shaping the cavity side of an anterior restoration, b) a second tool path for shaping the incisal side of a restoration, and c) a third tool path for reducing the diameter of the stem. In one embodiment, the nesting step of positioning the first stem end adjacent the restoration design comprises aligning the fitting surface of the restoration design in the direction of the flow of coolant from the milling machine.

In a further embodiment, the method comprises generating machining instructions having at least five tool paths comprising: a) a first tool path for machining a first portion of the cavity side of the restoration that is opposite the stem, b) a second tool path for machining a second portion of the cavity side of the restoration that is adjacent the stem, c) a third tool path for machining a first portion of the incisal side of the restoration corresponding to the labial surface, d) a fourth tool path for machining a second portion of the incisal side of the restoration corresponding to the lingual surface, and e) a fifth tool path for reducing the diameter of the stem. In one embodiment, tool paths for machining a portion of the cavity side and the incisal side are lacing tool paths.

In a further embodiment, the method comprises splitting first and second incisal tool paths along a line that is substantially parallel the incisal edge, wherein the first incisal side comprises the labial surface adjacent the incisal edge and a second incisal side comprises the lingual surface adjacent the incisal edge. Optionally, the lacing tool paths comprise sequential lines that are parallel the incisal edge for the labial surface and the lingual surface. In a further embodiment, a tool path for milling a portion of the cavity side opposite the stem encompasses a portion of the vestibular surface and the fitting surface. In another embodiment, the fifth tool path for reducing the stem comprises a rotary tool path having simultaneous movement in a Y-axis direction, wherein the tool path is contained within a border in the rotary direction.

The order of machining steps and tool paths may vary, and terms such as first and second, for example, as used in first tool path, second tool path, third tool path, first machine step, second machine step, and so forth, are used for descriptive convenience, and should not be connoted as indicative of a specific order of steps unless otherwise noted.

Figure 17:
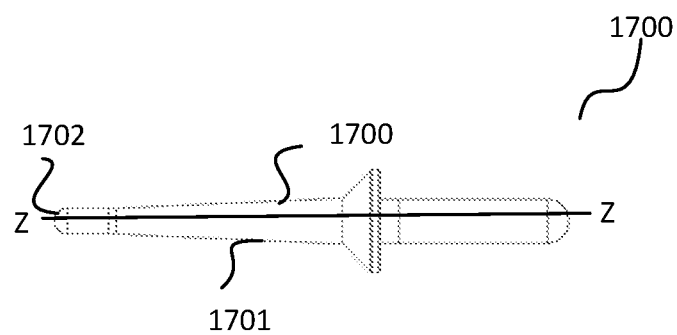
FIG. 17. A side view of a graphic representation of a grinding tool according to one embodiment.

Material feed rates may be individually controlled for each machine step. Machining parameters may comprise different material feed rates for incisal side and cavity side tool paths. Machining parameters may be implemented on a 3+1 axis CNC machine to shape a finished anterior dental restoration from a ceramic block comprised of material having a Vickers hardness value greater than or equal to about HV4 GPa with a single grinding tool comprising an alloy coating embedded with diamonds in a chair-side application. In another embodiment, the custom dental restoration may be machined in a 3+2, or 4, or 5 axis machine. Corresponding 3+2 or 4 or 5 axis machining cycles may be used to specify a tool axis angle relative to the tool contact normal of the machined surface either directly from the CAD data of the restoration, or indirectly using a separate tool axis drive surface interpolated from the original CAD data. In a further embodiment, more than one grinding tool may be used for grinding the preform. Multiple grinding tools may be used sequentially, for example, for roughing and finishing, or multiple grinding tools may be used simultaneously, on opposite surfaces of the preform. A suitable chair-side milling machine includes, but is not limited to the TS150™ chair-side milling system (IOS Technologies, San Diego, CA), and an exemplary grinding tool (300) suitable for use herein is illustrated in FIG. 17.

The methods described herein provide enhanced machining in chairside applications for preform materials having a Vickers hardness value greater than or equal to about HV 4 GPa (Vickers macro-hardness), or a value in the range of HV 4 GPa to HV 20 GPa (i.e., HV 4 GPa to HV 20 GPa), when measured according to the method provided herein. Alternatively, preform materials have a Vickers Hardness value between HV 5 GPa and HV 15 GPa, or between HV 11 GPa and HV 14 GPa. Preform body materials comprising hardness values within this range may include metals, such as cobalt chrome, glass and glass ceramics, such as lithium silicate and lithium disilicate, and ceramic materials, including sintered ceramics comprising alumina and zirconia.

Dental restoration materials, including but not limited to commercially available dental glass, glass ceramic or ceramic, or combinations thereof, may be used for making the preforms that are machinable by the methods described herein. Ceramic materials may comprise zirconia, alumina, yttria, hafnium oxide, tantalum oxide, titanium oxide, niobium oxide and mixtures thereof. Zirconia ceramic materials include materials comprised predominantly of zirconia, including those materials in which zirconia is present in an amount of about 85% to about 100% weight percent of the ceramic material. Zirconia ceramics may comprise zirconia, stabilized zirconia, such as tetragonal, stabilized zirconia, and mixtures thereof. Yttria-stabilized zirconia may comprise about 3 mol % to about 6 mol % yttria, or about 2 mol % to about 7 mol % yttria. Examples of stabilized zirconia suitable for use herein include, but are not limited to, yttria-stabilized zirconia commercially available from (for example, through Tosoh USA, as TZ-3Y grades). Methods form making dental ceramics also suitable for use herein may be found in commonly owned U.S. Pat. No. 8,298,329, which is hereby incorporated herein in its entirety.

The preform body may be made from unsintered materials shaped into an intermediate form having substantially the same geometry as the sintered preform, but with enlarged dimensions to accommodate shrinkage upon sintering, where necessary. Suitable unsintered ceramic materials may be made into blocks by processes including molding and pressing, including biaxial or iso-static pressing, and may optionally comprise binders and processing aids. Ceramic blocks may be shaded so that the sintered preforms have the color of natural or artificial dentition, requiring no further coloring after formation of the dental restoration. Coloring agents may be incorporated during block formation to more closely match the appearance of natural or commercially available artificial dentition than uncolored or unshaded ceramic materials. Optionally, ceramic powder may be processed into blocks by slip casting processes, including processes described in commonly owned U.S. Patent Publication No. 2009/0115084, U.S. Pat. No. 9,365,459, and U.S. Pat. No. 9,434,651, each of which is hereby incorporated herein by reference in the entirety. Pre-sintered ceramic blocks suitable for use in making intermediate shaped forms include commercially available ceramic milling blocks including those sold under the trade name BruxZir® (for example, BruxZir® Shaded 16 Milling Blanks, Glidewell Direct, Irvine, CA). In some embodiments, the theoretical maximum density of fully sintered zirconia ceramics is between about 5.9 g/cm$^3$ to about 6.1 g/cm$^3$, or for example, or about 6.08 g/cm$^3$.

A unitary preform may be shaped from a from a single continuous green-state block or pre-sintered ceramic block, requiring no separate attachment step for attaching the stem and/or attaching member to the preform body. Alternatively, the preform may be made by known molding processes, including injection molding. The intermediate shaped form may be sintered to a density greater than about 95% of the theoretical maximum density by known sintering protocols. Sintered zirconia ceramic preforms may have densities greater than about 95%, or greater than about 98% or greater than about 99%, or greater than about 99.5%, of the maximum theoretical density of the ceramic body.

The preform body comprises materials that are shapeable into dental restorations in chair-side applications by the methods described herein, that have acceptable strength properties for use in anterior, posterior or both anterior and posterior dental restoration applications, without additional post-shaping processing steps to alter the material strength properties after shaping, such as by sintering. Sintered preforms may comprise zirconia ceramic materials that have high flexural strength, including strength values greater than about 400 MPa, or greater than about 500 MPa, or greater than about 600 MPa, or greater than about 800 MPA, when tested by a flexural strength test method for zirconia materials as outlined in ISO 6872:2008, as measured and calculated according to the 3 point flexural strength test described for Dentistry—Ceramic Materials, or as provided herein.

Flexure strength testing may be performed on sintered test materials using the Instron-Flexural Strength test method for zirconia materials as outlined in ISO 6872:2008. Test bars may be prepared by cutting bisque materials taking into consideration the targeted dimensions of the sintered test bars and the enlargement factor (E.F.) of the material, as follows: starting thickness=3 mm×E.F.; starting width=4 mm×E.F.; starting length=55 mm×E.F. The cut, bisque bars were sintered substantially according to the sintering profile provided by manufacturer of the bisque material. Flexural strength data was measured and calculated according to the 3 point flexural strength test described in ISO (International Standard) 6872 Dentistry—Ceramic Materials.

Preform materials may be tested for hardness using a Vickers Hardness (macro-hardness test). Hardness numbers (HV) may be calculated as described in ISO-6507, or by determining the ratio of F/A where F is the force applied in kg/m$^2$ and A is the surface area of the resulting indentation (mm$^2$). HV numbers may be converted to SI units and reported in units, HV GPa, as follows: H(GPa)= 0.009817HV.

Dental restorations may be made by grinding sintered ceramic preforms using grinding tools instead of traditional milling tools because of the material hardness which renders typical milling tools unsuitable in certain embodiments. Grinding tools having a diamond coating, including nickel plated tools embedded with diamonds, are suitable for use herein. A grinding tool (1700) having a shank (1701) and tool tip (1702), for example as illustrated in FIG. 17, comprises an embedded diamond coating on the shank (1701) and tip. Diamonds suitable for use herein include blocky or friable diamonds having an average size in the range of about 90 micron to about 250 micron, or an average size in the range of about 107 micron to about 250 micron, or an average size in the range of about 120 micron to about 250 micron, or for example, an average size in the range of about 120 micron to about 180 micron. Suitable diamond coatings include those in which at least 50% of the diamonds are embedded by a metal alloy layer for more than half the height of the diamond, for example, as determined by SEM analysis. Grinding tools having a coating in which diamonds are embedded in a metal alloy to a depth of about 50% to 95% of the average diamond size, or about 60% to about 95% of the diamond size, or to about 80% to about 95% of the diamond size are useful for shaping preforms made from materials such as fully sintered zirconia preforms, or preforms comprising materials having the hardness values described herein. In some embodiments, grinding tools have a diamond coated shank with a metal alloy layer having thickness that is greater than about 50% of the diamond grit size (e.g., in microns), or greater than about 60%, or greater than about 70%, or greater than about 80%, or greater than 90%, or between about 60% and 90%, or between about 80% and 100%, of the diamond grit size (e.g., in microns). In one embodiment, a grinding tool has a diamond coated shank comprising a diamond size in the range of 126 grit to 181 grit, and a nickel alloy layer having a thickness that is greater than or equal to about 70% of the diamond grit size (in microns).

Examples 1 and 2

Sintered zirconia preforms and polymer mandrels were prepared having interference fit connections, and maximum load of the connection was measured and averaged for multiple samples.

Figure 7A:
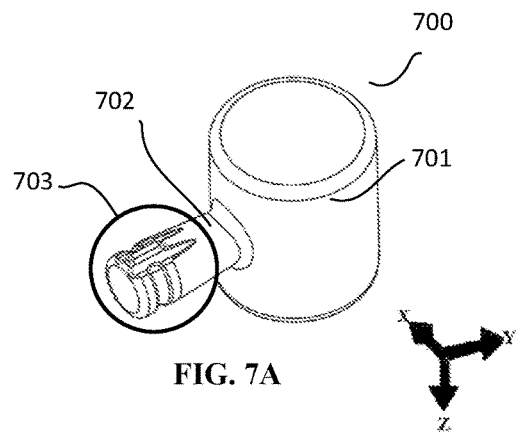
FIGS. 7A, 7B and 7C. Graphical representations of a preform according to one embodiment.
Figure 7B:
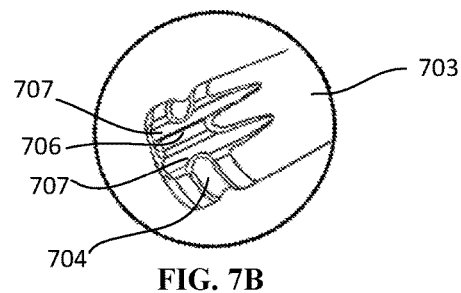
Figure 7C:
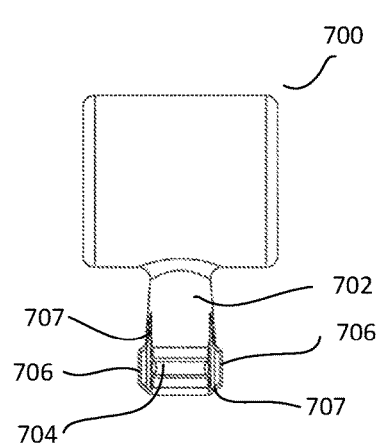

Forty-six sintered zirconia ceramic preforms were prepared having a configuration substantially the same as FIGS. 7A and 7B, by milling and sintering yttria-stabilized zirconia bisque stage blocks. Forty-six nylon mandrels were made having the configuration substantially the same as FIG. 6. The sintered zirconia preform stem ends comprised two opposing ridges projecting above the outer diameter of the smooth curved portions of the stem end, with channels (707) on either side of the ridges (706) and a concentric groove between ridges. The inner surface of the top of the mandrels accessible through a hole was smooth and the inner diameter of each was smaller than the diameter of the stem measured through the ridges. A two-part adhesive (UHU PLUS 300, USU GmbH, Bühl, Germany) was applied to the outer surface of the stem end filling channels for half of the samples. The stems were inserted into the mandrels by applying pressure to deform the inner surface of the softer mandrel material with the ridges to achieve an interference fit, and glued samples were allowed to dry at room temperature.

The strength of the connection between mandrel and preform was tested on an Instron machine measuring pulling (axial) force reported as Max Load (N). Glued samples had an average maximum load of 521 N (23 samples) and non-glued samples had an average maximum load of 245 N (23 samples).

We claim:

1. A method for making an anterior dental restoration from a fully sintered zirconia preform, comprising
obtaining an anterior dental restoration virtual design and a virtual model of a preform body, wherein the anterior dental restoration virtual design comprises and incisal edge and the preform body comprises a cylindrical shape having a stem projecting from a curved outer surface;
nesting the anterior dental restoration virtual design within the virtual model of the preform;
detecting a topmost point on the incisal edge of the anterior dental restoration virtual design and using the topmost point to define a line of separation that is either parallel to or orthogonal to the incisal edge of the anterior dental restoration virtual design;
generating machining instructions for shaping an anterior dental restoration from a fully sintered zirconia preform, said machining instructions comprising:
a first tool path located on a first side of the line of separation, and
a second tool path located on a second side of the line of separation; and
machining the fully sintered zirconia preform using the machining instructions.

2. The method of claim 1, wherein the line of separation is defined by:
forming an angle from lines intersecting a vertex at a distance above the topmost point and extending to points on opposite outer surfaces of the anterior dental restoration design.

3. The method of claim 2, wherein the line of separation is defined by:
selecting points on opposite outer surfaces of the anterior dental restoration design that are defined using the smallest available angle.

4. The method of claim 2, wherein the distance above the topmost point is 1 mm.

5. The method of claim 2, wherein the line of separation is defined by:
drawing a line between the points on opposite outer surfaces of the anterior dental restoration design to define a line of separation that is parallel to the incisal edge of the anterior dental restoration.

6. The method of claim 2, wherein the line of separation is defined by:
drawing a line between the points on opposite outer surfaces of the anterior dental restoration design to define a line of separation that is orthogonal to the incisal edge of the anterior dental restoration.

7. The method of claim 1, wherein the first tool path is provided for a labial surface of the anterior dental restoration and the second tool path is provided for a lingual surface of the anterior dental restoration.

8. The method of claim 7, wherein the first and second tool paths have sequential tool path line lengths parallel to the incisal edge of the anterior dental restoration that extend between a mesial side and a distal side of the anterior dental restoration.

9. The method of claim 7, wherein the first and second tool paths follow a parting line between the incisal edge and a gingival margin of the anterior dental restoration.

10. The method of claim 1, wherein the machining instructions further comprise:
a rotary tool path around a first end of the stem that is located adjacent the anterior dental restoration.

11. The method of claim 10, wherein the rotary tool path defines a plurality of horizontal slices that are perpendicular to a length axis of the stem.

12. The method of claim 10, wherein the rotary tool path incorporates movement in a Y-axis direction that simultaneously follows a surface of the anterior dental restoration in the region of the stem.

* * * * *